United States Patent [19]

Janese

[11] Patent Number: 4,781,202

[45] Date of Patent: Nov. 1, 1988

[54] BIOPSY CANNULA

[76] Inventor: Woodrow W. Janese, 2806 N. Navaro, Suite M, Victoria, Tex. 79901

[21] Appl. No.: 91,800

[22] Filed: Aug. 31, 1987

[51] Int. Cl.⁴ .................................................. A61B 17/34
[52] U.S. Cl. ........................................ 128/754; 128/310
[58] Field of Search ............................ 128/749, 751–754, 128/305.1, 310; 604/93, 164

[56] References Cited

U.S. PATENT DOCUMENTS

| | | | |
|---|---|---|---|
| 2,198,319 | 4/1940 | Silverman | 128/754 |
| 3,001,522 | 9/1961 | Silverman | 128/754 |
| 3,007,471 | 11/1961 | McClure et al. | 128/754 |
| 3,173,414 | 3/1965 | Guillant | 128/752 |
| 3,590,808 | 7/1971 | Muller | 128/752 |
| 3,595,217 | 7/1971 | Rheinfrank | 128/754 |
| 4,243,048 | 1/1981 | Griffin | 128/751 |
| 4,461,305 | 7/1984 | Cibley | 128/754 |
| 4,600,014 | 7/1986 | Beraha | 128/754 |
| 4,651,752 | 3/1987 | Fuerst | 128/754 |

FOREIGN PATENT DOCUMENTS 251138  1/1970  U.S.S.R. ............................. 128/754

Primary Examiner—Kyle L. Howell
Assistant Examiner—Randy Citrin
Attorney, Agent, or Firm—Fulbright & Jaworski

[57] ABSTRACT

The present invention provides a biopsy device for obtaining tissue samples while preserving the relational aspects of the tissue substructure and architecture. The biopsy device comprises a cannula housing and a spring activated sharpened blade which is slideable engageable with the cannula housing.

8 Claims, 3 Drawing Sheets

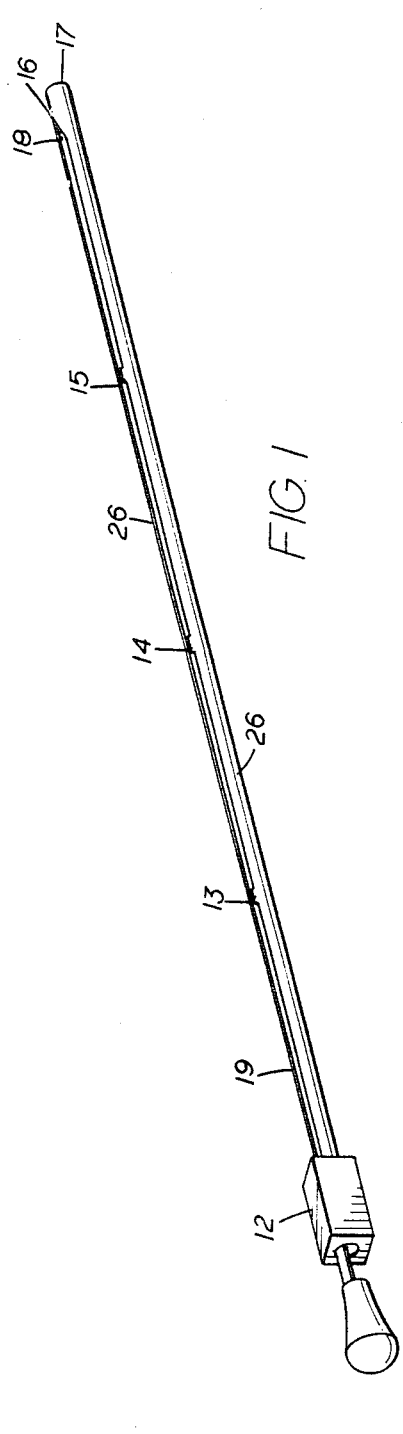
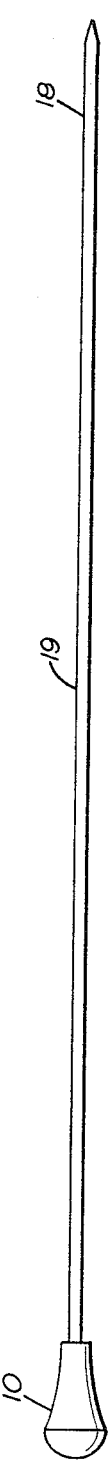
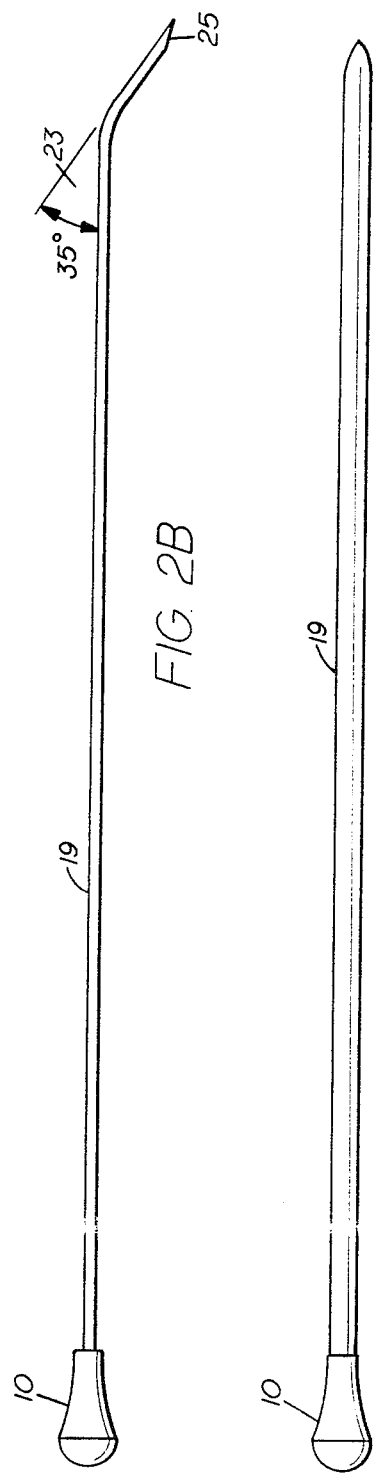

BIOPSY CANNULA

BACKGROUND OF THE INVENTION

1. Field of the Invention

The present invention relates to a medical instrument that can obtain a tissue sample. More particularly, the invention relates to a biopsy needle.

2. Description of the Background Art

In the treatment of disease or pathological conditions it is often necessary to examine a sample of tissue to detect pathological changes in order to accurately diagnose and render proper treatment. In many instances, a knowledge of the exact cytoarchitecture of the tissue is critical to diagnosis of the specific pathological condition. When such tissue samples are removed by use of an aspirating needle such as that disclosed is U.S. Pat. No. 3,595,217 to Rheinfrank, the relational aspects of tissue substructure and infrastructure are not maintained.

There is a growing need for a device capable of obtaining brain tissue samples, for example, which samples retain the relational aspects of the brain tissue architecture. Biopsies of brain tissues are often performed for the diagnosis and localization of peripherally located brain tumors, infectious diseases, such as viral infections, including herpes simplex of the temporal lobe, Acquired Immune Difficiency Syndrome with toxoplasmosis, SSPE (Subacute sclerosing panencephalitis), neurolipidoses (storage diseases) and Alzheimer's disease. Accurate diagnosis in disease states such as those cited depend on the examination of brain tissue obtained by biopsy. The accuracy of the diagnosis will often depend upon preservation in the tissue sample of the relational aspects of the tissue architecture.

Alzheimer's disease is considered one of the most pressing problems in the 1980s, being the fourth largest cause of death in the United States. Based on pathological evaluations, it is estimated that half of all the patients in the United States with dementia have untreatable Alzheimer's disease. On the other hand, biopsy for prognosis information is important. Ten to 20 percent of all dementias or 20-40% of the remaining 50% can be successfully treated if diagnosed correctly. An accurate tissue biopsy will detect these treatable cases and be efficacious.

The neuropathologist uses paraffin embedding and paraffin microtome sectioning and frozen sectioning. Using various techniques, multiple stains according to the cellular material of interest are used for study.

The study is examined grossly under the light microscope ($\times 40$, $\times 100$, $\times 400$, $\times 1000$); changes of the neurons, fibrous connective tissue, glia, and vascular structures are observed. Nerve cell loss is important. Abnormal interneuronal material can indicate abnormal stored material: (1) neurolipidoses (ganglioside—Tay Sachs disease, Sphingomyelin—Neimann-Pick disease); (2) degeneration processes (senility pigment—lipofuscin, Alzheimer's neurofibrillary degeneration, Parkinson's disease—Lewy bodies and various viral inculsion bodies, e.g., SSPE, rabies).

Special techniques involve transmission electron microscopy, histoenzymological examinations of fresh brain and immunostaining using peroxidase antibodies.

Tissue lesions can be demonstrated by hemorrhages, atrophy, necrosis, cerebral edema, demyelination, inflammatory lesions, and connective tissue and vascular changes. Artifacts caused by unnecessary "rough handling" of brain tissue as demonstrated by biopsy suctioning, biopsy crushing, biopsy stretching, and biopsy ripping can erroneously cause hemorrhages, cerebral swelling, vascular injury and cell injury and interfere with diagnostic accuracy.

The brain biopsy information is correlated with clinical data and ancillary investigations.

A number of devices have been developed to obtain biopsy of tissue from individuals from areas such as the brain. Biopsy cannulas are often used by neurosurgeons, in some cases with the aid of fluoroscopy, computerized tomography, Magnetic Resonance Imaging, or ultrasonography. Among the devices which were available prior to the present invention are a cannula which uses suction by a syringe to obtain a biopsy; a device in which forceps protrude from a cannula to obtain a sample, and are withdrawn; and a device which comprises a spiral cutting tip in a cannula to obtain biopsy samples. In devices such as the foregoing examples, the samples are traumatized, significantly affecting the quality and accuracy of the pathologic review. Suction of brain tissue into a needle disrupts the relational architecture of the tissue and may also disrupt the cytoarchitecture, as will compression caused by forceps or the grinding action of a spiral cutting edge. In addition, the trauma caused by removal of tissue samples by devices such as those described often leads to hemorrhage in the area from which the tissue sample was removed and causes protracted recovery of the patient.

Other biopsy devices have been devised which operate along principles described above. For example, U.S. Pat. No. 4,461,305 discloses an automated biopsy device which has a rotary mounted cutting blade which severs the tissue for extracting biopsy tissue from the female uterine cervix. A biopsy device developed to primarily obtain endocervical canal tissue samples was disclosed in U.S. Pat. No. 4,243,048, which has a non-metal "nose cone" which provides a guiding protuberance and a hollow tubular member telescopically fitted on the shaft which has an annular cutting element on the distal end and a hollow inner chamber which receives the tissue specimen. U.S. Pat. No. 3,590,808 discloses a biopsy device for use in the gastrointestinal tract in which a tissue sample is drawn into the hollow end of the device by vacuum and a pneumatically operable knife severs the biopsy sample. U.S. Pat. No. 3,173,414 discloses a combination of a biopsy probe and endoscope which utilizes a suction pump to draw in the severed tissue sample.

Examples of needle biopsy devices such as are shown in U.S. Pat. No. 2,198,319 and U.S. Pat. No. 3,001,522 disclose needles which are sharpened to sever the tissue and provide space within the shaft of the needle for storing the selected tissue and which may incorporate a gripping mechanism. U.S. Pat. No. 4,600,014 discloses a transrectal prostate biopsy device which is an improvement on the Travenol TRU-CUT ® biopsy needle.

It is an object of the present invention to provide a biopsy device for obtaining biopsy samples from tissues, and preferably from brain tissue, wherein the tissue removed from the individual retains the relational aspects of the tissue substructure and architecture. It is a further object of the present invention to devise a biopsy device which is capable of removing a tissue sample for maximally accurate pathological examination and be capable of minimizing cerebral injury, swelling, or arterial vessel injury, and subsequent blood clot formation.

SUMMARY OF THE INVENTION

A biopsy device is provided which acts as a cutting tool which cores out a cylinder of tissue with minimal pressure, which will allow the preservation of the tissue and cytoarchitecture. The device is composed of a round thin-walled needle or cannula and a thin blade which is housed in an axial slot in the outer circumference of the needle or cannula housing. An opening extends coaxially the length of the needle or cannula from the proximal to the distal ends of said cannula housing. The blade slides along channel guides in the axial slot and is initially locked into a position parallel to the length of the needle by the channel guides. The spring-loaded blade, prior to engagement for cutting, is held at an angle parallel to the shaft of the needle by engaging the distal end of the blade with a shoulder (blade restraint or blade rest) on the Periferal surface of the needle shaft. Once the needle or cannula is inserted to the desired depth, the blade is engaged for tissue cutting action by withdrawing the blade to release it from the distal blade rest, which releases the blade tip from its parallel position. The spring-loaded blade in its preferred position curves, in a preferred embodiment at a 35° angle, and thus when released from its distal perch, will curve toward the floor of the shaft of the needle. As the surgeon pushes the hub of the blade inward in a longitudinal direction, the blade will sever the tissue, and at the same time, close off the distal channel of the needle. The needle is then withdrawn, containing the non-crushed biopsy sample of approximately 0.4–0.8 cc. The needle also will push aside cerebral arteries as it advances, preventing hemorrhage of these arteries and removing the vessels from the cutting field. Since the cutting by the blade is done within the needle or cannula shaft itself, there will again be no chance to damage or sever the cerebral vessels adjacent the blade during tissue engagement and cutting of the tissue. One advantage of the present invention over tissue sampling devices previously available is that the present invention cuts a cylinder of tissue and then amputates the base of the cylinder by a sharp blade cut, which prevents tissue tearing which occurred when tissue samples were extracted by suction or by stretching the base until tissue tearing occurred. Tissue tearing at times ruptured arteries and caused tissue injuries several centimeters removed from the biopsy region, which in critical neural anatomical areas would cause severe morbidity or mortality.

A further advantage of the present invention is that relatively large biopsy samples, approximately 0.4–0.8 cc, can be obtained, as opposed to the small samples of about 0.05 to 0.1 cc which could be obtained from other biopsy needles. The device of the present invention is also safer to use than those which rely on suction to sever the tissues from the area being biopsied in that the suction caused trauma to the surrounding tissue, which resulted in brain swelling and intracerebral hematoma, which can cause stroke and/or death in the individual from whom the tissue is being removed.

An additional advantage of the present invention is the simple construction which will increase the ease of manufacture and of sterilization of the device. The two-part construction consists of a blade and a cannula housing. The blade may be replaced after each biopsy, insuring that a sharp blade will prevent tissue tearing with every biopsy taken. In addition, the cannula housing is reusable, which will increase the economy of use of this biopsy device.

The biopsy device of the present invention can also be applied to organs other than the brain, such as kidney, liver, bowel, testes, lung, muscle, prostate, breast, cervix and ovary, which organs are often biopsied and for which the relational tissue architecture must be maintained for an accurate diagnosis of pathological states. The size of the needles, both in gauge and length, in which the blade is adapted, can be varied to suit individual organ and the special requirements of each type of biopsy specimen required. The advantages and embodiments of the present invention will become apparent from the following description when read in conjunction with the drawings.

In a preferred embodiment, the present invention comprises a biopsy needle comprising a generally cylindrical housing having proximal and distal ends and a coaxially extending opening therethrough, the housing having an axial slot therein, adjacent, but spaced from, the distal end, support means on the housing for retaining a blade in position in the slot, shoulder means near the distal end of said housing adjacent to the distal end of said axial slot for holding the distal end of a flexible blade out of the opening but allowing the distal end of the blade to contract into said opening for cutting a specimen when the blade is disengaged relative to said shoulder, and a flexible blade having proximal and distal ends, positioned in said axial slot of said housing and slideably engageable with the housing, the distal end of the blade being sharpened and spring actuated for contracting into the opening of the housing when disengaged from said shoulder means, wherein the width of said blade is fixed relative to the width of said axial slot such that said blade when engaged in said housing assumes a curvilinear shape.

BRIEF DESCRIPTION OF THE DRAWINGS

FIG. 1 is a prospective view of one embodiment of the biopsy needle of the present invention.

FIG. 2 is a lateral view of the guillotine blade with its blade restraint engaged, non-tissue-engaged (2A) and tissue engaged (2B) positions.

FIG. 3 is a superior view of the blade.

DETAILED DESCRIPTION OF THE PREFERRED EMBODIMENTS

Figure 4:
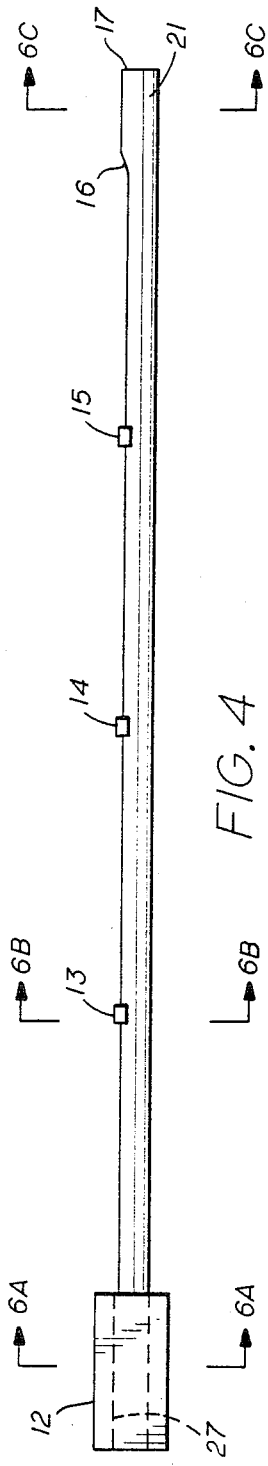
FIG. 4 is a lateral view of the cannula housing with three channel guides in which the blade in a semi-circular shape conforming to the rounded shape of the cannula housing, is inserted.
Figure 5:
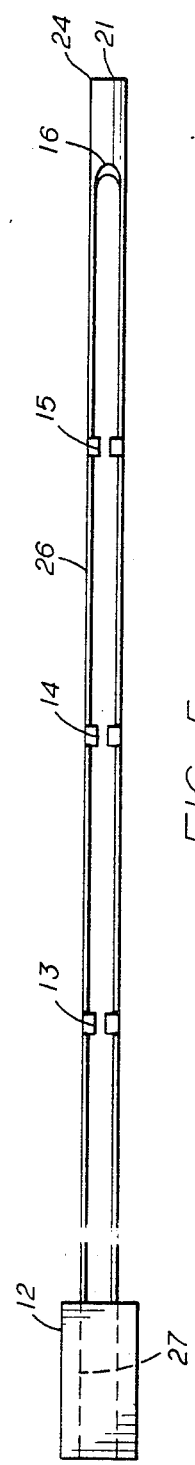
FIG. 5 is a superior view of the cannula housing.
Figure 6C:
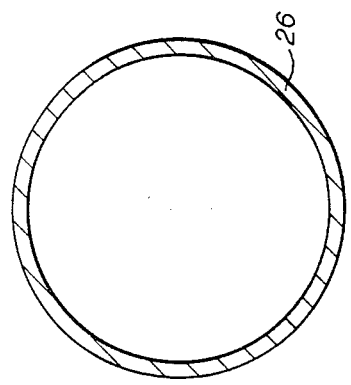
FIG. 6C is a transverse section of the cannula housing taken along the lines 6C—6C in the area where the guillotine blade impacts the floor of the distal housing of the cannula.
Figure 6B:
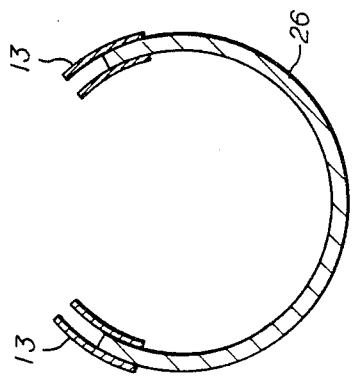
FIG. 6B is a transverse section of the cannula housing taken along the lines 6B—6B though a housing guide channel.
Figure 6A:
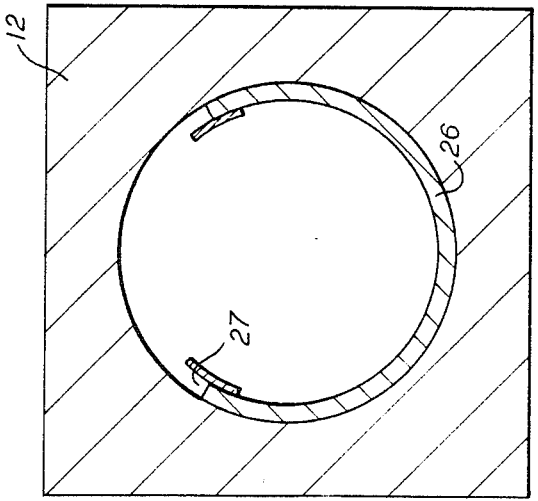
FIG. 6A is the transverse section on the cannula housing hub taken along the lines 6A—6A.

As shown in FIG. 1, a preferred embodiment of the biopsy needle of the present invention for use as a brain cannula, which comprises a blade 19, a blade hub 10, a cannula 26, a cannula hub 12, channel guides 13, 14 and 15, a blade restraint 16 on the superior edge of the cannula, a cannula cutting edge 17, a blade cutting edge 18. When the flexible blade 19 is inserted into the cannula housing 26, it conforms to a curvilinear shape to fit into the channel guide in the hub 27 and the channel guides 13, 14 and 15 of the cannula. The flexible blade is made to be spring actuated, in a preferred embodiment, by being prebent to form a leaf spring means for contracting into the channel or opening which extends coaxially through the cannula housing. The blade, when it is not engaged by the blade restraint (16) of the cannula, ends flexibly at a 35° angle for a length of 12.7 mm at the distal portion in a preferred embodiment for use as a brain cannula. When the cutting blade is engaged in the blade restraint 16 of the cannula, the guillotine blade is straight, and non-engaged with respect to the tissue as can be seen in FIG. 2A, in which the cutting blade 19 is demonstrated in a lateral view in the spring-loaded resting position 2A (restraint engaged) and the tissue engaged position 2B. In a preferred embodiment, the blade restraint is a shoulder means located adjacent to, but not at, the distal end of the cannula housing at the distal end of the axial slot.

The guillotine blade is engaged in the cannula housing by contacting the guide channels 13, 14 and 15 seen in FIG. 4, and is held in the spring-loaded resting position by the blade restraint 16 on the superior surface 26a of the cannula 26.

Figure 7:
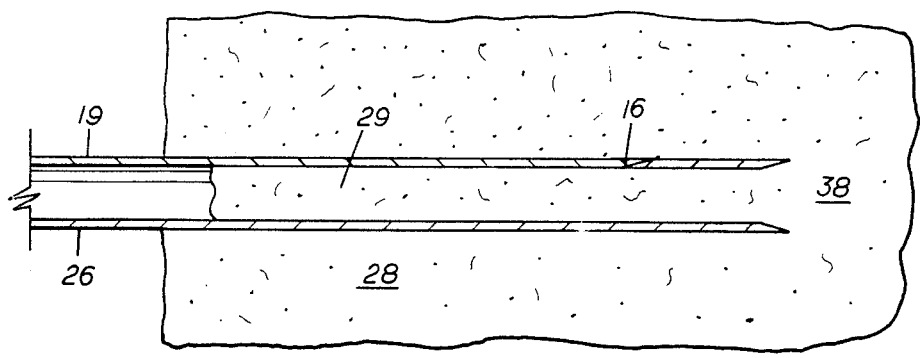
FIG. 7 is a cross-section of one embodiment of the invention, wherein the blade is non-tissue engaged and resting in the non-cutting position.
Figure 8:
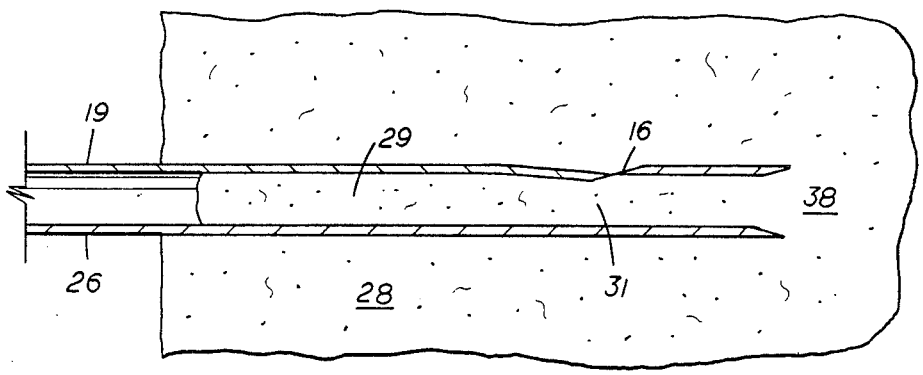
FIG. 8 is a cross-section of one embodiment of the invention after the blade has been withdrawn 1-2 mm, causing release of the blade and resultant engagement.
Figure 9:
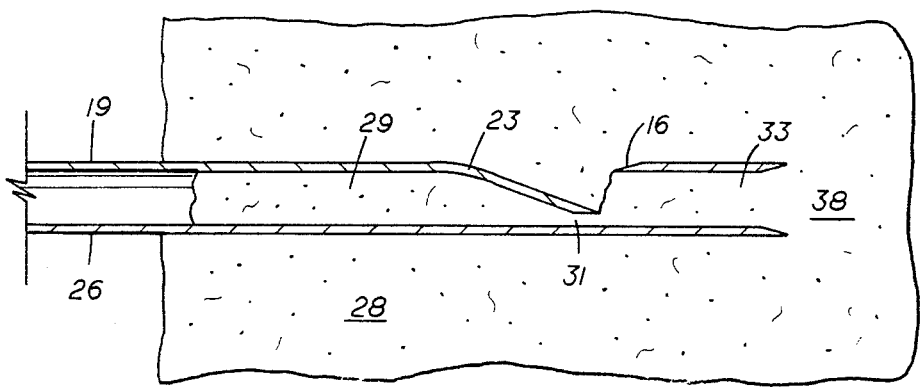
FIG. 9 is a cross-section of the invention after the "spring like" mechanism of the cutting blade begins impact and cutting of the tissue.
Figure 10:
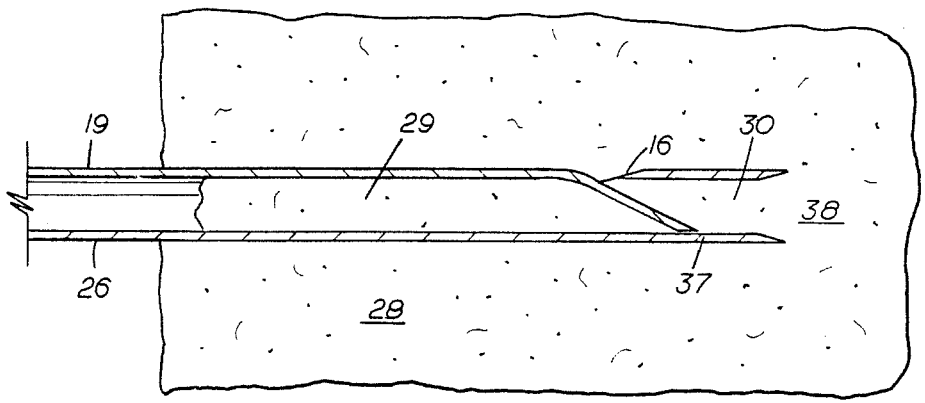
FIG. 10 is a cross-section of the biopsy needle of the present invention after the blade has been inserted distally a distance of approximately 5 to 7 mm, causing the blade to sever the tissue sample from the surrounding tissue wherein the tip of the blade rests on the floor of the cannula housing.

As seen in FIGS. 7, 8 and 9, when the blade is withdrawn 2 mm, and thereby released from the blade restraint 16 of the cannula, the kinetic energy of the spring-loaded blade (0.25-0.5 PSI) causes the blade to bend toward the cannula floor due to the 35° bend of the spring-loaded blade and causes the blade to contact the tissue within the cannula chamber. Then as the blade 19 is moved forward toward the distal end of the cannula housing by pressure on the blade hub 10, as seen in FIGS. 9 and 10 the cylinder of tissue within the cannula chamber is severed from the surrounding tissue. The blade is moved forward until the tip of the blade 18 contacts the floor of the cannula housing, at which time the tissue sample within the cannula is completely severed from the organ proper from which the organ sample is being taken. The organ being sample, in the preferred embodiment, the brain, remains quiescent. The cannula and blade, which now contain in the cannula chamber a section of brain tissue, is then carefully retracted from the brain with minimal injury due to the biopsy procedure.

The distal portion of the blade, when contacting the floor of the cannula housing, serves to keep the biopsy sample tissue in place in the cylinder until the sample is withdrawn from the body. After removal from the body, the blade is withdrawn and the cannula containing the biopsy specimen is placed in a solution appropriate for the diagnostic tests to be performed. The tissue sample is then gently removed from the cannula, while preserving the architecture of the sample.

It will be obvious to those of skill in the art that the biopsy needle of the present invention may be used to obtain tissue samples from other parts of the body besides the brain. It may be used on humans and animals alike. The length and diameters described in the present application, and the accompanying drawings, may be modified to suit particular applications and any such modifications will be seen by those of skill in the art to fall within the spirit and scope of the present invention.

What is claimed is:
1. A biopsy needle, comprising
    a hollow cylindrical housing having a proximal end and a cylindrical distal end and a coaxially extending cylindrical opening therethrough,
    the housing having an axial slot therein, adjacent, but spaced from, the distal end,
    support means on the housing for retaining a blade in position in the slot,
    shoulder means near the cylindrical distal end of said housing adjacent to the distal end of said axial slot for holding the distal end of a flexible blade out of the opening but allowing the distal end of the blade to contract into said opening for cutting a specimen within the needle when the blade is disengaged relative to said shoulder, and
    a flexible blade, having proximal and distal ends, movably positioned in said axial slot of said housing and slideably engageable with the support means, wherein said blade can slide in an axial direction to disengage from said shoulder means when slid towards the proximal end of said housing, the distal end of the blade being sharpened and spring actuated by being prebent to form a leaf spring means for contracting into the opening of the housing when disengaged from said shoulder means, the blade being curved in cross section and with the housing forming a cylindrical portion of said opening for receiving a cylindrical biopsy sample.

2. The biopsy needle of claim 1 wherein said housing is generally cylindrical.

3. The biopsy needle of claims 1 or 2 wherein said slot is discontinuous at the proximal and distal ends of said housing.

4. The biopsy needle of claim 2 including
    a hub connected to the housing at the proximal end of said housing.

5. The biopsy needle of claim 2 wherein the spring actuation of said blade is limited to the distal end portion of the blade.

6. The invention of claim 5 wherein said blade includes a distal cutting edge shaped to conform to the inside surface of the distal end of the housing when pressed there against.

7. The biopsy needle of claim 2 wherein the support means constitute axial grooves in the periphery of the housing and wherein the blade is slideably mounted in the grooves.

8. The invention of claim 7 wherein the grooves are discontinuous.

* * * * *